(12) United States Patent
Peterson et al.

(10) Patent No.: US 10,500,404 B2
(45) Date of Patent: Dec. 10, 2019

(54) UNIVERSALLY ADAPTABLE MODULE FOR DEFIBRILLATOR MONITORS

(71) Applicant: Physio-Control, Inc., Redmond, WA (US)

(72) Inventors: Kenneth J. Peterson, Bellevue, WA (US); John C. Daynes, Redmond, WA (US); Mitchell A. Smith, Sammamish, WA (US); Moira M. Galvin, Kirkland, WA (US); David B. Stewart, Carnation, WA (US); Jennifer G. Jensen, Mill Creek, WA (US); Matthew L. Bielstein, Seattle, WA (US); Cathlene D. Buchanan, Shoreline, WA (US); Jeffrey S. Edwards, Bellingham, WA (US); Clayton M. Young, Redmond, WA (US); Karen K. Langman, Kirkland, WA (US); Bethany J. Johnson, Snoqualmie, WA (US)

(73) Assignee: Physio-Control, Inc., Redmond, WA (US)

(*) Notice: Subject to any disclaimer, the term of this patent is extended or adjusted under 35 U.S.C. 154(b) by 0 days.

(21) Appl. No.: 15/132,113

(22) Filed: Apr. 18, 2016

(65) Prior Publication Data

US 2016/0303389 A1 Oct. 20, 2016

Related U.S. Application Data

(60) Provisional application No. 62/148,707, filed on Apr. 16, 2015.

(51) Int. Cl.
*A61N 1/39* (2006.01)
*A61B 5/0205* (2006.01)
*A61B 5/0402* (2006.01)
*A61B 5/0476* (2006.01)
*A61B 5/145* (2006.01)

(Continued)

(52) U.S. Cl.
CPC ........ *A61N 1/3925* (2013.01); *A61B 5/02055* (2013.01); *A61N 1/3968* (2013.01); *A61N 1/3993* (2013.01); *A61B 5/021* (2013.01); *A61B 5/0402* (2013.01); *A61B 5/0476* (2013.01); *A61B 5/0836* (2013.01); *A61B 5/14542* (2013.01); *A61B 2560/0443* (2013.01); *A61B 2562/227* (2013.01)

(58) Field of Classification Search
CPC ... A61N 1/3925; A61N 1/3968; A61N 1/3993
See application file for complete search history.

(56) References Cited

U.S. PATENT DOCUMENTS

| | | | |
|---|---|---|---|
| 8,880,168 B2 * | 11/2014 | Pearce | A61N 1/39 607/5 |
| 2006/0041278 A1 * | 2/2006 | Cohen | A61N 1/39 607/5 |

* cited by examiner

*Primary Examiner* — Paula J Stice
(74) *Attorney, Agent, or Firm* — Lane Powell PC

(57) ABSTRACT

An adaptable healthcare module that is coupleable to one or more defibrillator devices is disclosed. The adaptable health care module includes a healthcare coupling to assist with treatment and/or monitoring of a patient. The healthcare coupling can be active while decoupling the adaptable healthcare module from a first defibrillator device and coupling to a second defibrillator device. The coupling of the adaptable healthcare module includes a mechanical engagement, between the adaptable healthcare module and the defibrillator device, to retain the adaptable healthcare module to the defibrillator device.

12 Claims, 7 Drawing Sheets

(51) Int. Cl.
*A61B 5/083* (2006.01)
*A61B 5/021* (2006.01)

UNIVERSALLY ADAPTABLE MODULE FOR DEFIBRILLATOR MONITORS

RELATED APPLICATION

This application claims benefit of priority to U.S. Provisional Patent Application Ser. No. 62/148,707 filed on Apr. 16, 2015, titled RE-USABLE MODULE FOR MULTIPLE VERSATILE TYPES OF DEFIBRILLATOR MONITORS, which is incorporated herein by reference in its entirety.

BACKGROUND

Unless otherwise indicated herein, the approaches described in this section are not prior art to the claims in this application and are not admitted to be prior art by inclusion in this section.

As integration of functionalities in devices increase, more and more devices are being capable of a wide variety of functionalities. For example, in the health related field, a health related electronic device may be capable of providing the functionality of treating and monitoring a patient for a wide variety of health related applications. An example of a health related device having a wide variety of functionalities may include a health related device for treatment of a heart condition. For example, a heart condition that may be experienced by a patient, who has a heart experiencing some condition such as, but not limited to, an arrhythmia, which may lead to a condition known as sudden cardiac arrest (SCA). In an SCA condition, the heart may fail to pump blood effectively, and as a result, death may occur. An example type of arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amount of blood or may not pump blood at all, which may eventually lead to death.

A healthcare related device may be utilized to help treat VF by defibrillating the heart. An example of a healthcare related device may be a monitor or a cardioverter defibrillator device, which may be referred to as a defibrillator or a defibrillator device. A defibrillator device may be capable of providing an electrical signal, commonly in the form of an electric shock, to the heart in an arrhythmia condition, such as a tachycardia, for example, a ventricular tachycardia (VT) or ventricular fibrillation (VF). The defibrillator device may provide the electrical signal to a heart externally (i.e., through the surface of a body) via accessories commonly known as electrodes. Commonly in the form of a pad, as the name may imply, the electrode may facilitate transfer of the electrical signal from the defibrillator device to the heart through the surface of the body.

In addition to the capability of defibrillating a patient's heart, the defibrillator device may be capable of providing a wide variety of health related treatments. Additionally, the defibrillator device may be capable of determining a wide variety of health related information about the patient (e.g., by monitoring and/or measuring health related activities of the person). In order for the defibrillator device to determine the information, the defibrillator device may be communicatively coupled to various peripheral components. For example, a health monitoring device may include the capabilities of monitoring a person's oxygen saturation level. In order to determine the person's oxygen saturation level, a component such as a sensor may be communicatively coupled to the defibrillator device with the sensor being attached to the patient.

In another example, the defibrillator device may include electrocardiography (ECG) capabilities. In order to use the defibrillator device as an ECG device, the ECG electrodes may be attached to the patient.

As may be appreciated, the above described examples of capabilities of the defibrillator device are but just a couple of examples, and the defibrillator device may include a wide variety of capabilities for a wide variety of applications. For example the defibrillator device may have capabilities of determining and monitoring activity related to a patient's circulatory system, where a patient's blood pressure may be measured with a pneumatic related component such as, but not limited to, a blood pressure cuff.

The example capabilities described may be facilitated by various connectors such as, but not limited to, electrical connectors and/or pneumatic connectors. As a patient may be moved from one defibrillator and/or monitoring device having some capabilities to another defibrillator and/or monitoring device having some different and/or more capabilities, the various connectors may be disconnected from one defibrillator device and reconnected to the other defibrillator device. Alternatively, the various connectors from one defibrillator device may be detached from the patient, and connectors from the other defibrillator device may be attached to the patient. As may be appreciated, disconnecting and reconnecting and/or detaching and attaching may cause an interruption in treatment and/or monitoring.

SUMMARY

The present disclosure describes example methods, where an example method may include a method of coupling an adaptable healthcare module with a defibrillator device. The example method may include receiving an indication of a coupling with the defibrillator device, establishing communication with the coupled defibrillator device, determining capable functionalities of the coupled defibrillator device, and facilitating utilization of the determined capable functionalities of the coupled defibrillator device.

The present disclosure describes example healthcare systems. An example healthcare system may include a first defibrillator device and an adaptable healthcare module. The adaptable healthcare module may be coupled with the first defibrillator device. The example healthcare system may include a coupling control module. The coupling control module may be included the adaptable healthcare module. The example healthcare system may include a processor. The processor may be included in the adaptable healthcare module and be communicatively coupled to the coupling control module. The example healthcare system may additionally include a healthcare coupling. The health care coupling may be included in the adaptable healthcare module and may be configured to facilitate treatment of and/or monitoring of a patient. Under the control of the processor, the coupling control module may be configured to facilitate continual utilization of the healthcare coupling while the adaptable healthcare module is decoupled from the first defibrillator device and/or while the adaptable healthcare module is coupled to a second defibrillator device.

The present disclosure describes example adaptable healthcare modules. An example adaptable healthcare module may include an adaptable healthcare module configured to be decoupleable from a first defibrillator device and be coupleable to a second defibrillator device. The example adaptable healthcare module may include a power supply and a processor. The processor may be communicatively coupled to the power supply. The example adaptable healthcare module may include a storage medium. The storage medium may be communicatively coupled to the processor and may be configured to store healthcare information associated with a patient. The example adaptable healthcare module may include a coupling control module communicatively coupled to the processor. Additionally, the example adaptable healthcare module may include a healthcare coupling. The healthcare coupling may be communicatively coupled to the coupling control module. Under the control of the processor, the coupling control module may be configured to facilitate utilization of the healthcare coupling while the adaptable healthcare module is coupled to the first defibrillator device, while the adaptable healthcare module is decoupled from the first defibrillator device, and/or while the adaptable healthcare module is coupled to the second defibrillator device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

Figure 1:
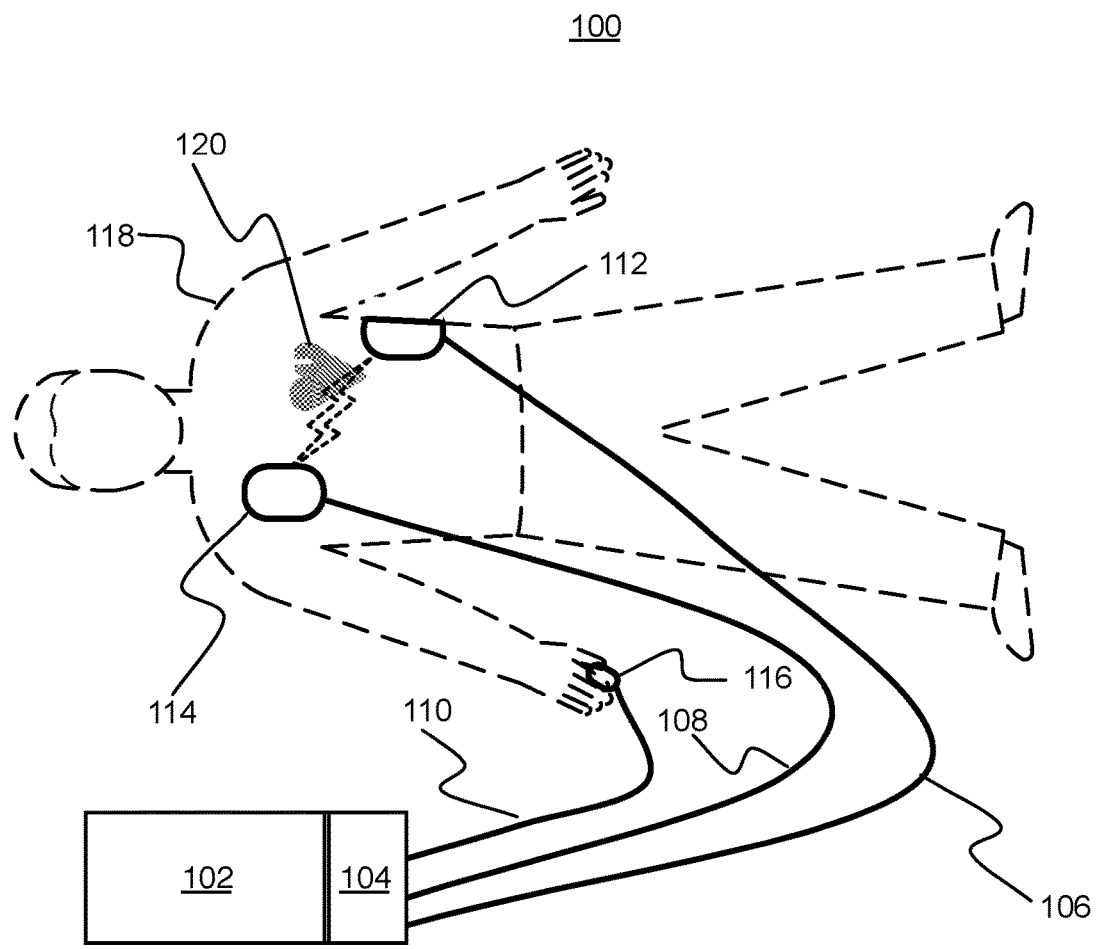
FIG. 1 illustrates a block diagram of an example system in accordance with various embodiments.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and systems related to a universally adaptable module for a defibrillator monitor.

As devices become more integrated, a single device may be capable of providing numerous functionalities. For example, in the healthcare related field, a single healthcare related device such as, but not limited to, a healthcare monitoring device, may have capabilities of providing a wide range of functionalities. Some examples of these functionalities may include healthcare related functionalities such as, but not limited to, measuring/monitoring a patient's oxygen saturation level ($SpO_2$) via a pulse oximeter type device, a patient's heart activity (ECG), a patient's brain activity such as, but not limited to electroencephalography (EEG), measuring/monitoring a patient's concentration or partial pressure of $CO_2$ such as, but not limited to, capnography capabilities (e.g., end-tidal carbon dioxide or $ETCO_2$), measuring/monitoring a patient's blood pressure such as, but not limited to, non-invasive blood pressure (NIBP) including continuous non-invasive arterial pressure (CNAP), invasive blood pressure, a patient's temperature, a patient's tissue oxygenation, and so forth. Some healthcare monitoring devices may include some or all of the example functionalities. However, more commonly, healthcare monitoring devices may include some of the functionality, while other healthcare monitoring devices may include some other or more sophisticated or specialized functionalities. In one example, a basic healthcare monitoring device may have the capability of providing limited functionality to defibrillation (e.g., automated external defibrillator or AED). In another example, a healthcare monitoring device may have the capability of providing basic life support (BLS) functionality. In yet another example, a healthcare monitoring device may include the capability to provide advanced life support (ALS) functionality. For the examples of BLS and ALS functionality, the healthcare monitoring device having the capability of providing BLS functionality may include defibrillator functionality and basic ECG functionality, while healthcare monitoring device having the capability of providing ALS functionality may include, in addition to defibrillator functionality and basic ECG functionality, advanced airway management functionality, advanced cardiac monitors, advanced cardiac life support equipment, blood glucose testing equipment, capnography equipment, and any wide range of treatment options. Even more advanced healthcare monitoring devices may have the capability of providing more advanced functionality such as, but not limited to, video related procedures (e.g., video laryngoscopy), intubation related procedures, ultra sound related procedures, telemedicine functionality (e.g., streaming video/audio with external imaging devices and built-in audio recording/playback devices), point of care lab analysis (e.g., blood and/or gas analysis), on-board electronic patient care recordation (e.g., electronic patient documentation), cardio pulmonary resuscitation feedback devices, ambient carbon monoxide monitoring, etc.

In order to facilitate utilization of this wide variety of functionality, while reducing interruption of treatment and/or monitoring of the patient, healthcare monitoring devices may be modular. Modular healthcare monitoring devices may also facilitate expansion of monitoring and communication functionality. An example of a healthcare monitoring device may be found in U.S. Pat. No. 7,957,798 titled "DEFIBRILLATOR/MONITOR SYSTEM HAVING A POD WITH LEADS CAPABLE OF WIRELESSLY COMMUNICATING", which is incorporated by reference in its entirety.

Hereon out, the disclosure may be described with respect to a healthcare monitoring device as a non-limiting example of a defibrillator device having capabilities of various functionalities. References may be made to a "defibrillator monitor" for healthcare devices, however it should be appreciated that healthcare monitoring devices may include a wide variety of healthcare monitoring devices, and accordingly, the claimed subject matter is not limited in these respects.

As previously described, defibrillators, cardioverters monitors may utilize various couplings to facilitate utilization of the various functionalities. A modular defibrillator device may facilitate new functionalities to be coupled to the modular defibrillator monitor, or a patient parameter module, or additional devices capable of specialized and/or limited functionality. For example, a modular defibrillator monitor may facilitate utilization of a wide range of healthcare monitoring devices such as, but not limited to, hospital crash cart equipment, hospital critical care transport equipment, BLS equipment, ALS equipment, etc., and accordingly, the claimed subject matter is not limited in these respects.

It should be noted that the referenced to a modular defibrillator monitor may include a defibrillator monitor capable of coupling, physically, electrically, and/or communicatively with a modular device via physical interface and/or wirelessly. As will be described in further detail, the coupling of the modular defib monitor with the modular device may facilitate utilization of a wide range of functionalities including a wide range of defibrillator monitors.

In one embodiment, the information contained within a defibrillator monitor can be delegated to an adaptable module which can then be detached or disengaged from the first monitor defibrillator device and coupled another device, such as another defibrillator, monitor, or another type of device to carry on with patient monitoring, specialized test data implementation and collection or some other type of therapy, which may include defibrillation therapy with a different defibrillator. The adaptable module is recognized and transferred to another device enabling a caregiver to provide seamless and time-saving continuation of patient care, monitoring, diagnosis, recommendations, and therapy. The adaptable module is capable of engaging with one or more other devices via either physical interface or wireless interface to transfer data in and/or out. Such module can connect to one device at a time or simultaneously engage with two or more devices. Such improvement is particularly necessary in the emergency field where every minute can make a big difference in the patient outcome.

The present subject matter discloses not just a modular design of a cardioverter defibrillator monitor system, but also the capability of one part of that system engaging with another part of a separate system, module, device. In one example, an adaptable module performs functions of a sensing, and/or monitoring module and measures patient parameters such as electrocardiogram (ECG), SPO2, NIBP, EtCO2, temperature, etc. The adaptable module can also be configured to comprise some features, capabilities and not others, depending on the user, market, patient's needs, specialization, hospital, or pre-hospital needs, etc. The adaptable module, which is now a monitoring and sensing module, can then be connected or coupled to another device capable of general or specialized functionality. The adaptable module is capable of coupling to one or more different types of devices, such as a defibrillator, a monitor, an ultrasound device, a laryngoscope, etc. The adaptable module, in a further embodiment, can provide a diagnosis and a recommendation for additional test or therapy and then be engaged with a particular device to carry out the next step. In a further embodiment, the adaptable module can wirelessly transfer information to another unit or a caregiver. Such modular approach and ability to couple with a variety of defibrillators, monitors, other medical devices while continuing patient care is highly desirable in the emergency situation but also in general, is desirable in the medical field.

Before describing in further detail the various embodiments disclosed herein, a non-limiting example scenario utilizing at least some various embodiments may be described in order to facilitate a more thorough understanding of the claimed subject matter. In one non-limiting example scenario, a person may be experiencing a VF (hereon out, "patient"). Emergency personnel may have been alerted and may arrive at the scene where the patient may be lying motionless. The first to respond may be emergency personnel trained as an emergency medical technician (EMT). Based at least upon their training, the EMT may have a BLS device (e.g., defibrillator monitor, also referred to as defib monitor). The EMT may remove a set of electrodes from the BLS device and attach the electrodes to the patient. Once the electrodes have been attached, the BLS device may be capable of monitoring the heart of the patient to determine the appropriate timing and charge for the administration of the electrical shock to the patient via the electrodes. After the defibrillating shock has been administered and the patient has been stabilized for VF, the EMT may attach electrodes for ECG monitoring via an electrical coupling (e.g., electrical leads). Additionally and/or alternatively, the EMT may attach a pulse oximeter device to the patient's finger, via an electrical coupling (e.g., an electrical lead), to monitor the patient's blood oxygen saturation level and pulse. In this example, the information received from the monitoring of the patient's ECG and/or the patient's blood oxygen saturation level and pulse may be recorded and/or displayed. As the patient is being monitored, the patient may be transported to a medical facility (e.g., hospital). Once the patient arrives at the hospital, the medical personnel may utilize more sophisticated healthcare monitoring devices such as, but not limited to an ALS device. Accordingly, the electrodes and pulse oximeter may be removed from the patient and a new set of electrodes and a new pulse oximeter coupled to the ALS device may be attached to the patient. Alternatively, the electrical leads for the electrodes and the pulse oximeter from the BLS device may be disconnected and reconnected at the ALS device. Either way, an interruption of monitoring, displaying, recording, and/or treatment of the patient may occur. However, as will be appreciated from the present disclosure, the monitoring and/or treatment of the patient may not be interrupted including uninterrupted recording and/or displaying of the patient's healthcare related information, in accordance with various embodiments. Additionally, in accordance with various embodiments, the information regarding the patient may be provided to another device and/or network seamlessly from one device to another and/or network.

Turning now to FIG. 1 (FIG. 1), where FIG. 1 illustrates a block diagram of an example system in accordance with various embodiments. In FIG. 1, system 100 may include a healthcare monitoring device 102 (hereon out, defibrillator monitor or defib monitor) and an adaptable healthcare module 104 (hereon out, adaptable module) coupled to the defib monitor 102. As shown, the adaptable module 104 may have one or more connectors 106, 108, & 110 (hereon out, leads) coupled to it. In FIG. 1, the leads 106 and 108 may be electrically coupled to electrodes 112 and 114. Additionally, the lead 110 may be electrically coupled to a pulse oximeter type device 116 (hereon out, oximeter). The electrodes 112 and 114 and the oximeter 116 may be attached to a patient 118. As previously described, the electrodes may comprise of the type that may be utilized to facilitate monitoring of the heart 120 of the patient 118 (e.g., ECG). The oximeter 116 may be utilized to facilitate monitoring of oxygen saturation levels (e.g., $SPO_2$) in the patient 118.

In one example, the information from the electrodes 112 and 114 and the oximeter 116 may be electrically communicated to the adaptable module 104 via the leads 106, 108, and 110. The leads 106, 108, and 110 may be physically coupled to the adaptable module 104 as healthcare couplings included in the adaptable module 104. The information received by the adaptable module 104 may be communicated directly to the defib monitor 102 for utilization by the defib monitor 102. Alternatively, the information received by the adaptable module 104 may be processed before being provided to the defib monitor 102, where the processing may help facilitate utilization by the defib monitor 102. Accordingly, the adaptable module 104 may have intelligent capabilities to determine appropriate communication with the defib monitor 102, in accordance with various embodiments. In another example, the information received by the adaptable module 104 may be utilized by the adaptable module 104 (e.g., store the information, display the information, etc.).

In FIG. 1, the adaptable module 104 having the capability of various functionalities (i.e., ECG and $SPO_2$) may be shown coupled to the defib monitor 102. However, the adaptable module 104 may be decoupled from the defib monitor 102 and may be coupled to another defib monitor 202 (shown in FIG. 2), in accordance with various embodiments.

Figure 2:
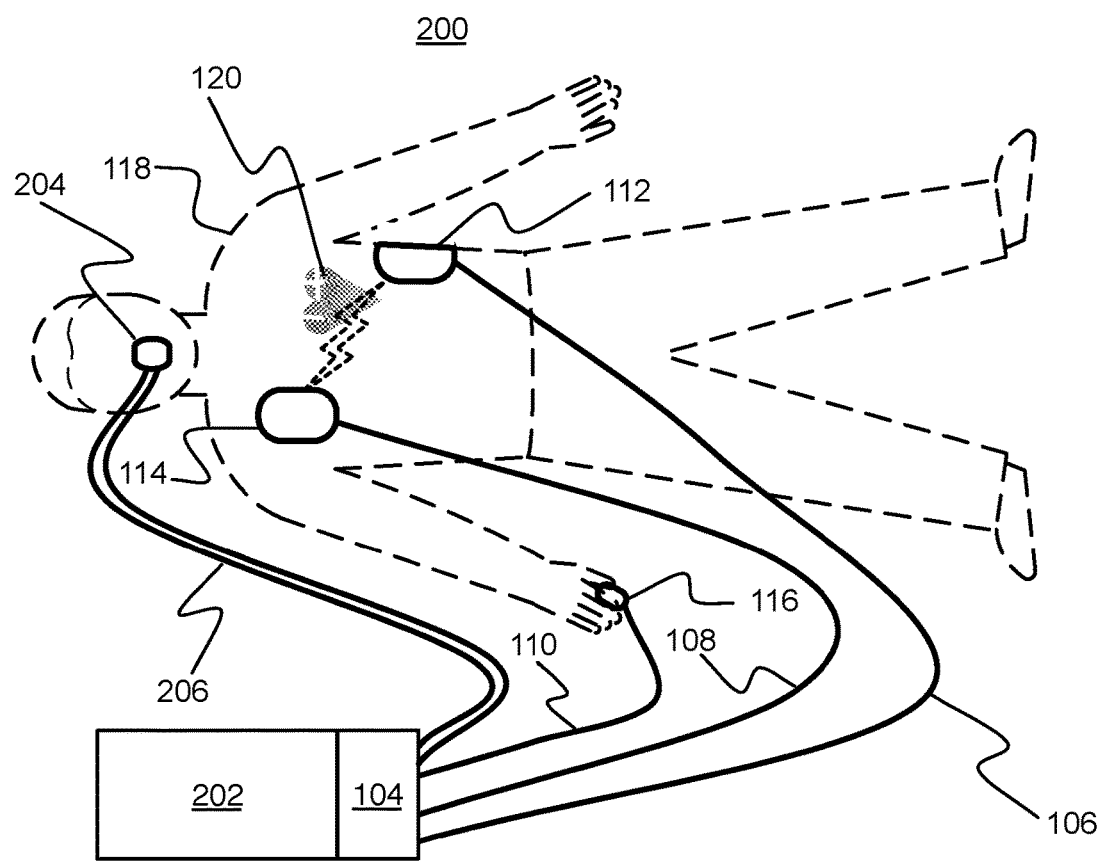
FIG. 2 illustrates a block diagram of an example system in accordance with various embodiments.

FIG. 2 (FIG. 2) illustrates a block diagram of an example system in accordance with various embodiments. In FIG. 2, system 200 may include another defib monitor 202 (hereon out, advanced defib monitor). The advanced defib monitor 202 may have the capability of advanced functionality as compared with the defib monitor 102 (shown in FIG. 1). As shown in FIG. 2, the adaptable module 104 (shown in FIG. 1) may be coupled with advanced defib monitor 202. The adaptable module 104 may facilitate utilization of the advanced functionality, in accordance with various embodiments.

Briefly turning back to FIG. 1, as previously described with respect to the non-limiting scenario, the defib monitor 102 may be capable of functionalities related to BLS. The patient 118 may be transported to a medical facility, where a medical personnel may utilize advanced defib monitors such as, but not limited to, hospital crash cart equipment, hospital critical care transport. Alternatively, an emergency personnel trained in ALS and/or advanced cardiovascular life support (ACLS) may have arrived at the scene to use the advanced defib monitor 202.

Continuing to refer to FIG. 2, in accordance with various embodiments, the adaptable module 104 may be decoupled from the defib monitor 102 (shown in FIG. 1) and coupled to the advanced defib monitor 202. Since the adaptable module 104 may be a self contained module (i.e., its own power supply, storage, intelligence, etc.), once the adaptable module 104 is decoupled from the defib monitor 102, the adaptable module 104 may continue to function to receive information from the patient (i.e., the electrodes 112 and 114 and the oximeter 116 may remain on the patient 118 and continue to provide information to the adaptable module 104 via the leads 106, 108, and 110), in accordance with various embodiments. In light of the present disclosure, it should be appreciated that even though some of the examples of decoupling may be described with respect to a user (e.g., EMT and/or medical personnel), decoupling may occur with in a wide variety of manners such as, but not limited to loss of wire connection, loss of pneumatic connection, wireless communication loss due to physical separation, environmental interference, and/or a control by the user to break the connection.

Shown in FIG. 2, the adaptable module 104 may be coupled to the advanced defib monitor 202 without interruption of information from the patient 118. Additionally, in FIG. 2, the advanced defib monitor 202 may have the capability of advanced functionality such as, but not limited to, capnography ($ETCO_2$), and accordingly, a capnography device 204 may be on the patient 118. The capnography device 204 may be coupled to the adaptable module 104 via a pneumatic tube 206, for example. As shown, the pneumatic tube 206 may be coupled to the adaptable module 104 at a healthcare coupling at the module 104 (e.g., a pneumatic coupling).

Figure 3:
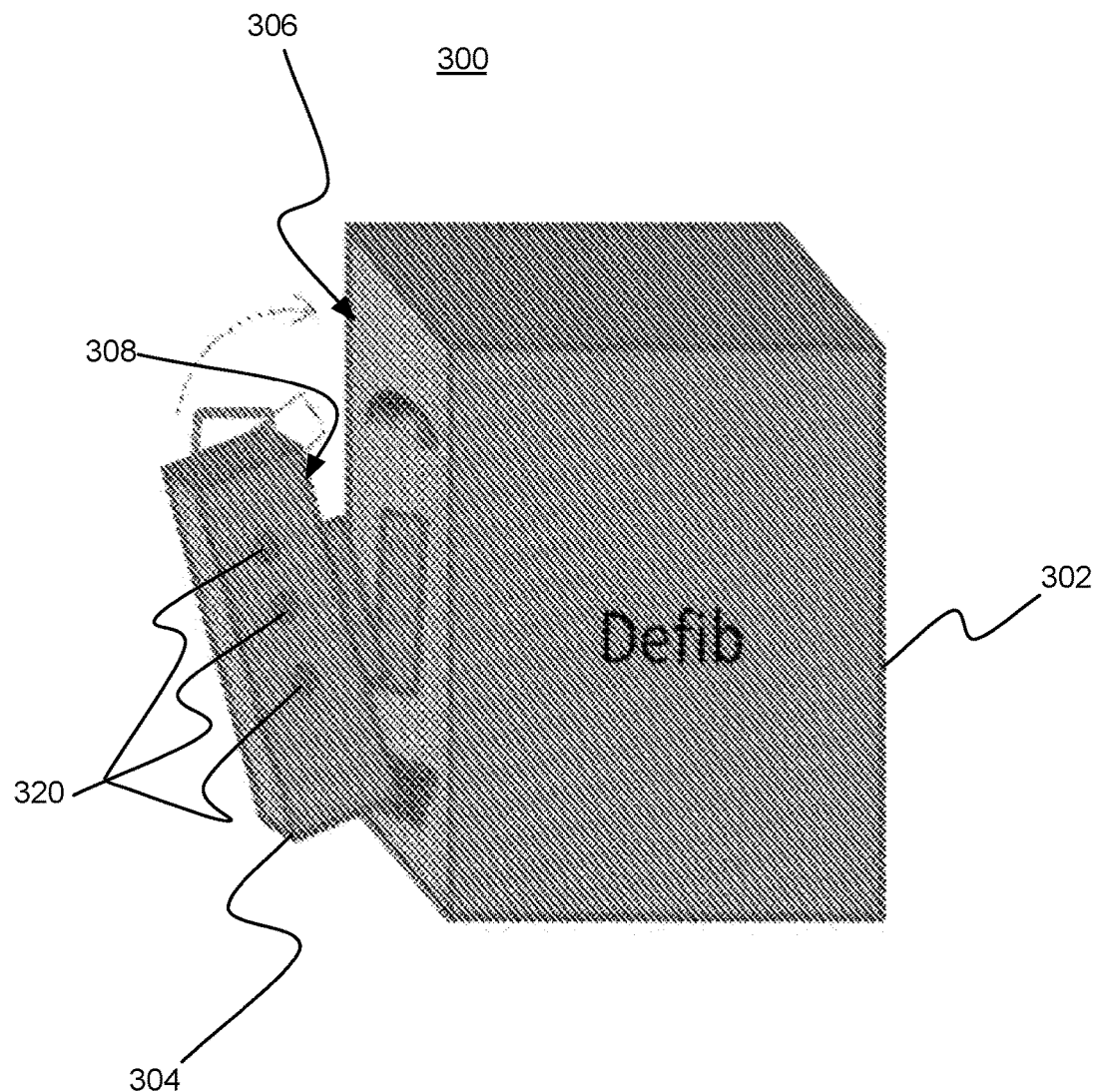
FIG. 3 illustrates a perspective view of an adaptable module and a defib monitor, in accordance with various embodiments.

FIG. 3 (FIG. 3) illustrates a perspective view of an adaptable module and a defib monitor, in accordance with various embodiments. In FIG. 3, system 300 may include a defib monitor 302 and an adaptable module 304. The adaptable module 304 may include a number of healthcare couplings 320. The healthcare couplings may facilitate coupling of various healthcare related monitoring and treatments (e.g., leads 106, 108, and 110 for electrodes 112 and 114 and oximeter 116 and/or the pneumatic tube 206 for capnography device 204). Additionally, shown in FIG. 3, the defib monitor 302 may have an interface 306 to facilitate coupling of the adaptable module 304. Accordingly, the adaptable module 304 may have a corresponding interface 308 to facilitate coupling with the defib monitor 302. The interfaces 306 and 308 may be of a mechanical interface type that may facilitate attachment and retention of the adaptable module 304 semi-permanently (e.g., use of attachment screws, bosses, fasteners, etc.) or user interchangeable (e.g., use of a mechanical latch for ease of release and attachment by hand) among a wide variety of defibrillator type devices. That is, the interfaces 306 and 308 may be implemented as a common interface among the wide variety of defibrillator type devices. The interfaces 308 and 308 may be configured to include electrical communicative capabilities. For example, the interfaces 306 and 308 may be capable of facilitating data communication between the defib monitor 302 and the adaptable module 304. Additionally, the interfaces 306 and 308 may be capable of facilitating power exchange (e.g., power from the defib monitor 302 to the adaptable module 304 and/or vice versa). The interfaces 306 and 308 may include a wide variety of power and/or data interfaces such as, but not limited to, a universal serial bus (USB) type including its various extensions (e.g., USB Type-C), Ethernet based type, peripheral component interconnect (PCI) type including its various extensions (e.g., PCI Express), etc., and accordingly, the claimed subject matter is not limited in these respects. Further, the interfaces 306 and 308 may include methodologies for electrical communications wirelessly such as, but not limited to, inductive power. It should be appreciated that alternative methodologies to mechanical and/or electrical type coupling between the adaptable module 304 and the defib monitor 302 may be utilized such as, but not limited to, a wireless coupling. A wireless coupling may be utilized to facilitate communication between the adaptable module 304 and the defib monitor 302, and additionally, the wireless coupling may be utilized to facilitate communication between any of the components of the system 300 (e.g., the defib monitor 302 and/or the adaptable module 304) with another device and/or network. For example, in the non-limiting scenario, when the patient arrives at a hospital, the adaptable module 304 may communicate the patient's healthcare information to the hospital's network and/or to the ALS device. For example, the ALS device would start receiving the patient's information seamlessly from the adaptable module 304 including during the transfer of the adaptable module 304 from the BLS device to the ALS device. The wireless communication may be facilitated via various communication algorithms and/or software.

The interfaces 306 and 308 may include methodologies to facilitate compliance with various healthcare related equipment standards such as, but not limited to, mechanical stresses (e.g., breakaway forces), electronic interference standards, vibration and rough handling standards, environmental protections (e.g., ingress protection rating or IP rating), etc., and accordingly, the claimed subject matter is not limited in these respects. For example, interfaces 306 and 308 may include magnetic forces to facilitate a stronger coupling.

Before turning to the details of an adaptable module, in light of the present disclosure, it should be appreciated that the adaptable modules may be self-contained (i.e., have their own enclosure) and may be designed to meet the physical and/or environmental requirements of healthcare related equipment, and in particular, pre-medical facility (pre-hospital). That is, the adaptable modules would at least meet the demanding environment of emergency response in a wide variety of environments and activities (e.g., outdoors in the snow, out on rough water, substantial rough ride on an aircraft, dropped from a predetermined height, impact requirement standards, etc.).

Figure 4:
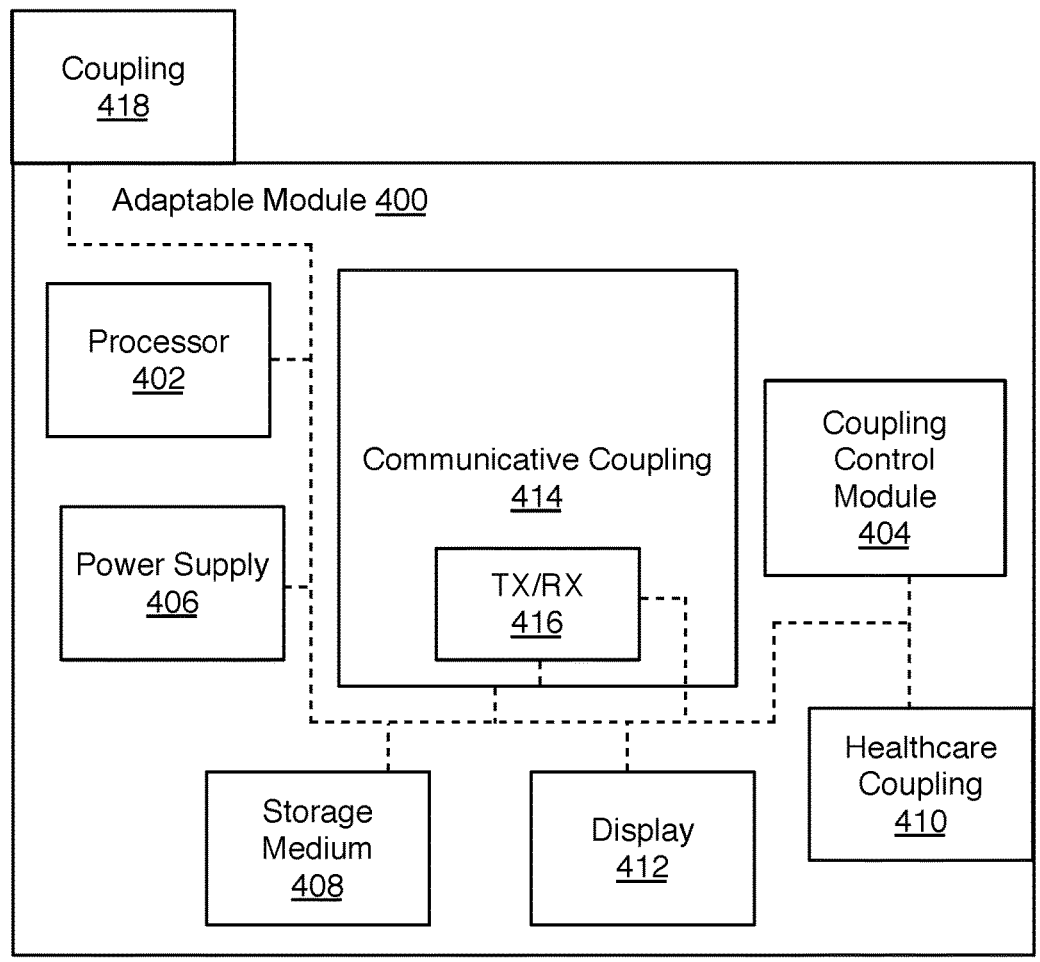
FIG. 4 illustrates a block diagram of an adaptable module, in accordance with various embodiments.

FIG. 4 (FIG. 4) illustrates a block diagram of an adaptable module, in accordance with various embodiments. In FIG. 4, an adaptable module 400 may include a processor 402, a coupling control module 404, a power supply 406, a storage medium 408, and a healthcare coupling 410. Under the control of the processor 402, the coupling control module 404, may be configured to facilitate utilization of the healthcare coupling 410, while the adaptable module 400 is coupled to a first defibrillator device, while the adaptable module 400 is decoupled from the first defibrillator device, and/or while the adaptable module is coupled to a second defibrillator device. For example, the healthcare coupling 410 may include a wide variety of healthcare couplings such as, but not limited to, couplings capable of facilitating functionalities related to pulse oximetry (peripheral oxygen saturation or $SPO_2$, carboxyhemoglobin or SpCO, methemoglobin or SPMet, or SpTH, tissue hemoglobin oxygen saturation or $StO_2$, muscle oxygen saturation or $SmO_2$, regional oxygen saturation or $rSO_2$, etc.), related to non-invasive blood pressure (NIBP) monitoring, related to end tidal carbon dioxide ($EtCO_2$) monitoring, invasive pressure (IP) monitoring, and/or temperature monitoring.

In accordance with various embodiments, referring back to FIGS. 1 and 2, the adaptable module 104 may include several healthcare couplings described. When the adaptable module 104 is attached to the first defib monitor 102 (e.g., BLS device), the healthcare couplings utilized by the first defib monitor 102 may be a subset of the healthcare couplings (e.g., electrodes 112 and 114 and oximeter 116). When the same adaptable module 104 is decoupled from the first defib monitor 102 and coupled to the advanced defib monitor 202 (e.g., ALS device), the adaptable module 104 may facilitate utilization of the functionality associated with additional healthcare couplings (e.g., capnography device 204). During the time that the adaptable module 104 is decoupled from the first defib monitor 102 and before being coupled to the advanced defib monitor 202, the adaptable module 104 would be continuously functioning to facilitate utilization of the healthcare coupling (e.g., electrodes 112 and 114 and oximeter 116) from the first defib monitor 102. This may be facilitated by the power supply 406 (shown in FIG. 4). Subsequently, when the adaptable module 104 is coupled to the advanced defib monitor 202, the adaptable module 104 would be continuously functioning to facilitate utilization of the healthcare coupling healthcare coupling (e.g., electrodes 112 and 114 and oximeter 116) from the first defib monitor 102, and additionally, the adaptable module 104 may function to facilitate utilization of any additional healthcare coupling healthcare coupling on the advanced defib monitor 202 (e.g., capnography device 204). In accordance with various embodiments, this process of coupling, decoupling, and recoupling of the adaptable module 104 to defib monitors may facilitate utilization of a single or limited number of adaptable modules for a wide variety of defib monitors having a wide variety of functionalities such as, but not limited to, the previously described.

Continuing with FIG. 4, in one example, the adaptable module 400 may include a display 412 device. The display device 412 may be configured to be utilized as a user interface to facilitate control of the operation of the adaptable module 400. In addition to or alternatively, the display device 412 may be configured to display various information including healthcare information of the patient 118 (shown in FIGS. 1 and 2). For example, the ECG readings from the patient 118 may be displayed on the display device 412. The display device 410 may include a wide variety of display device types such as, but not limited to, liquid crystal display (LCD) type devices, display devices utilizing light emitting diode (LED) technology including organic (OLED), display devices utilizing touch technology including active matrix (AMOLED), etc., and accordingly, the claimed subject matter is not limited in these respects.

As previously alluded to, the adaptable module 400 may include a communicative coupling module 414. The communicative coupling module 414 may include circuitry to facilitate communication with defib monitors and/or other healthcare related devices and/or networks. Referring back to FIGS. 1 and 2, the communicative coupling module 414 may facilitate communication with the first defib monitor 102 for the utilization of the healthcare couplings and for receiving information from the patient 118. Additionally, when the adaptable module 104 is coupled to the advanced defib monitor 202, the communicative coupling module 414 may facilitate communication with the advanced defib monitor 202 to facilitate determination of the capable functionalities of the advanced defib monitor 202 and configure itself accordingly (e.g., facilitate utilization of advanced functionalities such as, but not limited to, the capnography functionality).

In one example, the communicative coupling module 414 may include a transmit/receive (TX/RX) module 416, which may include circuitry to facilitate communication with defib monitors and/or other healthcare related devices and/or networks wirelessly. For example, the storage medium 408 may be configured to store the healthcare information of the patient 118, and this healthcare information may be transmitted (e.g., downloaded) to other devices and/or networks. The adaptive module may also transmit information related to the amount of power it has in its battery/power supply to the defib monitor. For example, this information indicate the percent of charge in the battery, or the amount of time the adaptive monitor may operate using its stored energy. In such embodiments, the defib monitor is configured to process this power information and provide an indication or display of this information to the operator of the defib monitor. For example, if the adaptive module is running low on power, it may transmit a "low power" message to the defib monitor so that appropriate action can be taken. As previously alluded to, the TX/RX module 416 may be configured to be capable of a wide variety of wireless communication methodologies such as, but not limited to, Wi-Fi, Bluetooth, near field communication (NFC), freespace optical, electromagnetic induction, cellular communication, global positioning system (GPS), Wi-Fi direct, etc., and any combination thereof. Accordingly, the claimed subject matter is not limited in these respects.

In FIG. 4, the adaptable module 400 may include a coupling module 418. As previously described, the coupling module 418 may facilitate mechanical attachment of the adaptable module 400 to a defib monitor. In one example, the coupling module 418 may include a rotatable latch. It should be appreciated that the coupling module 418 may include a wide variety of attachment methodologies such as, but not limited to, magnetic, fasteners, bolts, screws, Velcro, adhesive, etc., and/or any combination thereof. Accordingly, the claimed subject matter is not limited in these respects.

In the adaptable module 400, it is contemplated within the scope of the claimed subject matter that additional modules may be included for additional functionalities such as, but not limited to, scanner functionalities (e.g., bar codes and/or quick response codes), image capture functionality, audio functionality, etc., and any combination thereof. Some examples of image functionalities may include functionalities such as, but not limited to, ultrasound, video laryngoscope, body camera, cell phone camera, etc., and accordingly, the claimed subject matter is not limited in these respects. Some examples of scanning functionalities may include functionalities such as, but not limited to, bar code, magnetic strip, smart chip, etc., and accordingly, the claimed subject matter is not limited in these respects. Some examples of audio functionalities may be included in an adaptable module and/or in a defib monitor, and many forms of computing devices (e.g., tablet, mobile phone, laptop, desktop, server, etc.), and accordingly, the claimed subject matter is not limited in these respects.

Figure 5:
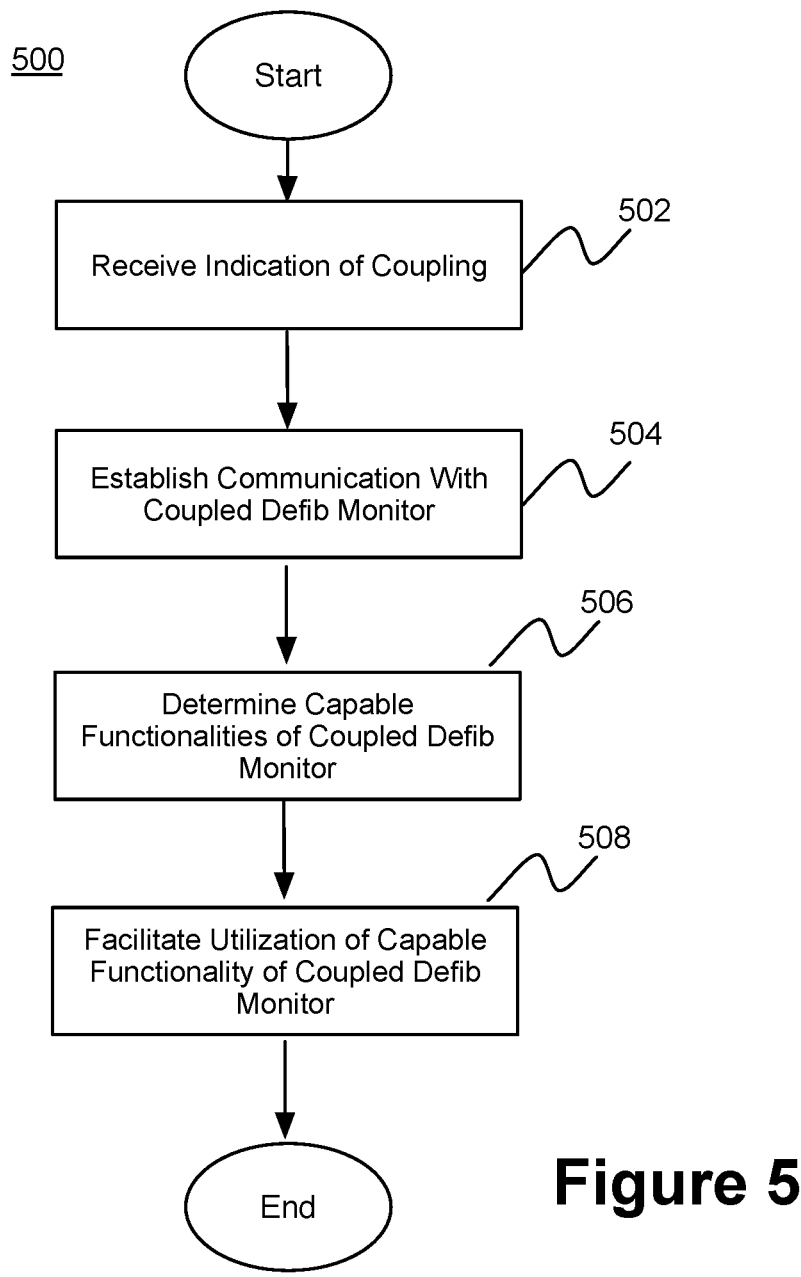
FIG. 5 illustrates an operational flow for an adaptable module, arranged in accordance with at least some embodiments described herein.

FIG. 5 (FIG. 5) illustrates an operational flow for an adaptable module, arranged in accordance with at least some embodiments described herein. In some portions of the description, illustrative implementations of the method are described with reference to the elements of the components described with respect to FIGS. 1-4. However, the described embodiments are not limited to these depictions. More specifically, some elements depicted in FIGS. 1-4 may be omitted from some implementations of the methods details herein. Furthermore, other elements not depicted in FIGS. 1-4 may be used to implement example methods detailed herein.

Additionally, FIG. 5 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 500 may be employed as part of an adaptable module. As previously described, an adaptable module may include a communicative module, a coupling module, and a coupling control module.

Beginning at block 502 ("Receive Indication of Coupling"), the communicative module 414 may detect a coupling of the adaptable module 104 with a defib monitor 102 and 202. The detection may be accomplished in a variety of manners. In one example, the adaptable module 104 may detect the defib monitor 102 and 202 and display information from the defib monitor 102 and 202 and any healthcare monitoring device/apparatus coupled to it. In another example, the defib monitor 102 and 202 may detect the presence of the adaptable module 104 and facilitate coupling of the defib monitor 102 and 202 with the adaptable module 104. In yet another example, the defib monitor 102 and 202 may wirelessly broadcast its availability, and if the adaptable module 104 detects/receives the broadcast, an attempt may be made by the adaptable module 104 to establish communication. In another example, the adaptable module may wirelessly broadcast its availability, and if the defib monitor 102 and 202 detects/receives the broadcast, an attempt may be made by the defib monitor 102 and 202 to establish communication. Establishing of the wireless communication may be performed in a wide variety of manners such as, but not limited to, timeout manners (e.g., if not established for approximately 30 second, the wireless communication may be determined to have failed).

Continuing from block 502 to 504 ("Establish Communication with Coupled Defib Monitor"), the communicative module 414 may establish communication with the defib monitor 102 and 202. As previously described, the established communication may be wired and/or wireless.

Once communication is established, the adaptable module 104 may determine the capable functionalities of the defib monitor 102 and 202 at block 506 ("Determine Capable Functionalities of Coupled Defib Monitor").

Once the capable functionalities of the defib monitor 102 and 202 is determined, under the control of the processor 402, the coupling control module 404 may facilitate the capable functionalities of the defib monitor 1202 and 202 (e.g., in addition to the ECG and oximeter, capnography) at block 508 ("Facilitate Capable Functionality of Coupled Defib Monitor"). That is, facilitate utilization of the healthcare couplings of the second defib 202.

Before moving on, it should be appreciated that the method may be similarly applicable to the initial coupling of the adaptable module 104 to any defib monitor 102, 202, and 300. As one may appreciate, the adaptable module 104 includes intelligence to couple with a wide range of healthcare devices having a wide range of healthcare functionalities.

In general, the operational flow described with respect to FIG. 5 and elsewhere herein may be implemented as a computer program product, executable on any suitable computing system, or the like. For example, a computer program product for facilitating utilization of an adaptable module. Example computer program products may be described with respect to FIG. 6 and elsewhere herein.

Figure 6:
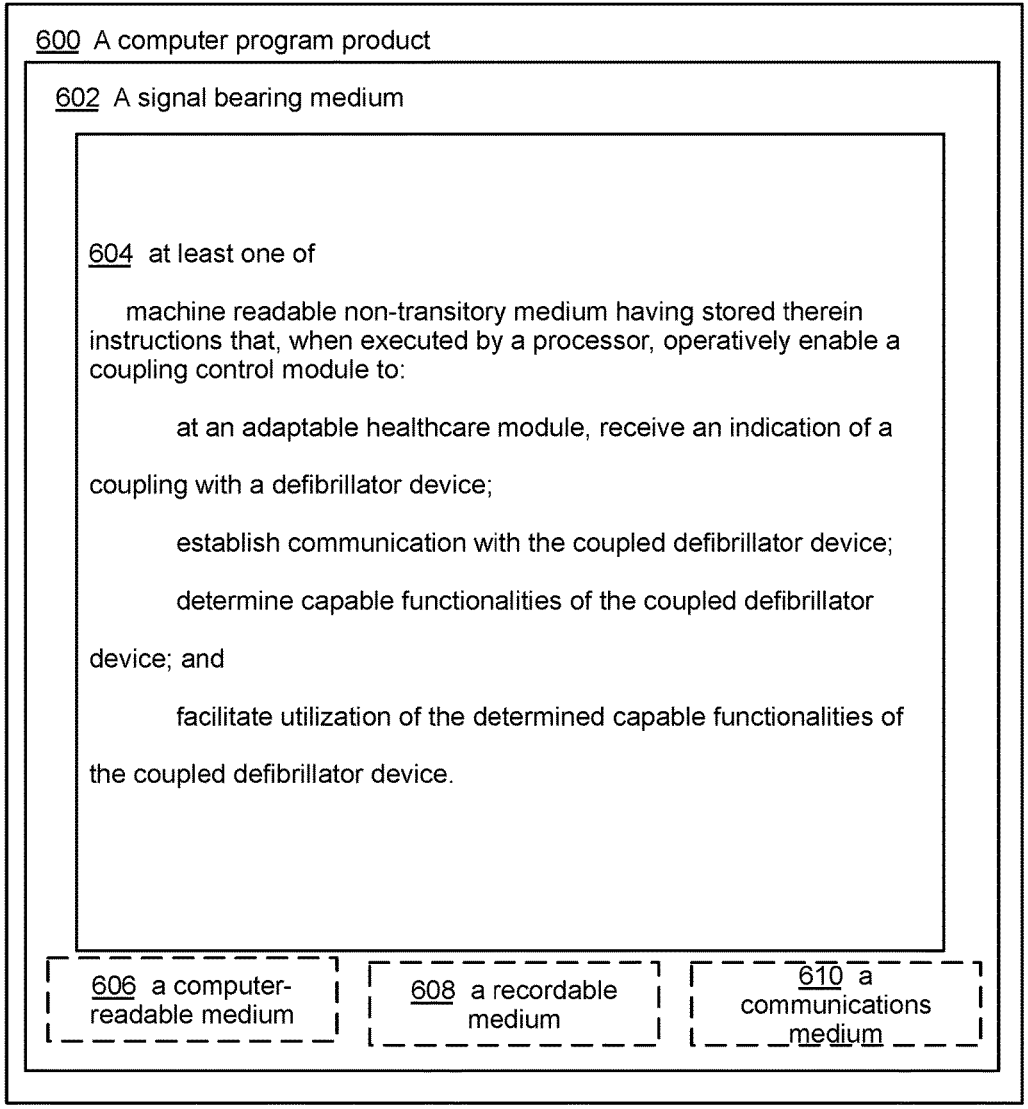
FIG. 6 illustrates an example computer program product 600, arranged in accordance with at least some embodiments described herein.

FIG. 6 (FIG. 6) illustrates an example computer program product 600, arranged in accordance with at least some embodiments described herein. Computer program product 600 may include machine readable non-transitory medium having stored therein instructions that, when executed, cause the machine to utilize an adaptable module, according to the processes and methods discussed herein. Computer program product 600 may include a signal bearing medium 602. Signal bearing medium 602 may include one or more machine-readable instructions 604, which, when executed by one or more processors, may operatively enable a computing device to provide the functionality described herein. In various examples, the devices discussed herein may use some or all of the machine-readable instructions.

In some examples, the machine readable instructions 604 may include instructions that, when executed, cause the machine to, at an adaptable module, receive an indication of a coupling with a defibrillator device, establish communication with the coupled defibrillator device, determine capable functionalities of the coupled defibrillator device, and facilitate utilization of the determined capable functionalities of the coupled defibrillator device.

In some implementations, signal bearing medium 602 may encompass a computer-readable medium 606, such as, but not limited to, a hard disk drive, a Compact Disc (CD), a Digital Versatile Disk (DVD), a digital tape, memory, etc. In some implementations, the signal bearing medium 602 may encompass a recordable medium 608 such as, but not limited to, memory, read/write (R/W) CDs, R/W DVDs, etc. In some implementations, the signal bearing medium 602 may encompass a communications medium 610 such as, but not limited to, a digital and/or an analog communication medium (e.g., a fiber optic cable, a waveguide, a wired communication link, a wireless communication link, etc.). In some examples, the signal bearing medium 602 may encompass a machine readable non-transitory medium.

Figure 7:
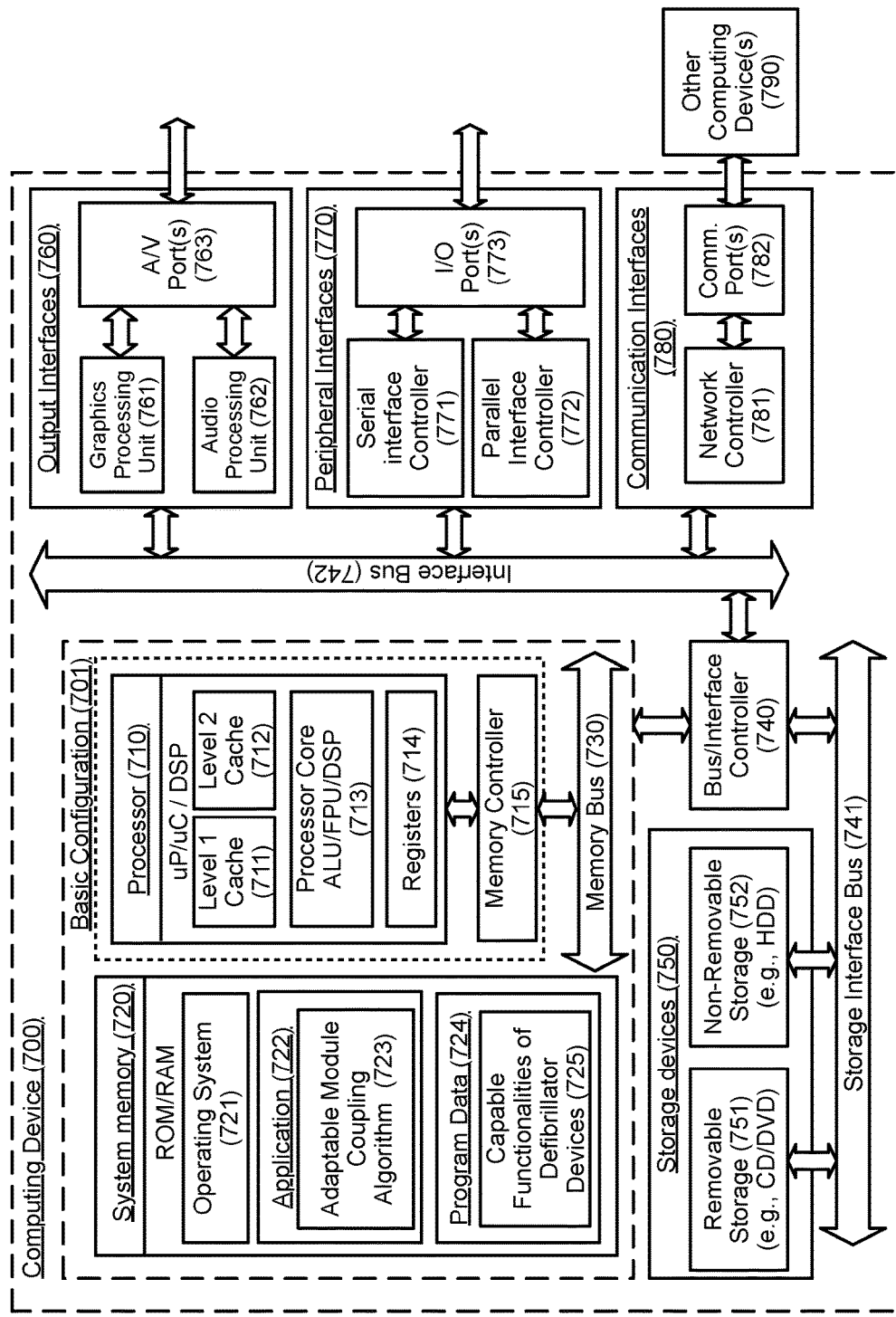
FIG. 7 is a block diagram illustrating an example computing device 700, such as might be embodied by a person skilled in the art, which is arranged in accordance with at least some embodiments of the present disclosure.

In general, the methods described with respect to FIG. 7 and elsewhere herein may be implemented in any suitable computing system. Example systems may be described with respect to FIG. 7 and elsewhere herein. In general, the system may be configured to facilitate utilization of an adaptable healthcare module, in accordance with various embodiments.

FIG. 7 (FIG. 7) is a block diagram illustrating an example computing device 700, such as might be embodied by a person skilled in the art, which is arranged in accordance with at least some embodiments of the present disclosure. In one example configuration 701, computing device 700 may include one or more processors 710 and system memory 720. A memory bus 730 may be used for communicating between the processor 710 and the system memory 720.

Depending on the desired configuration, processor 710 may be of any type including but not limited to a microprocessor (μP), a microcontroller (μC), a digital signal processor (DSP), or any combination thereof. Processor 710 may include one or more levels of caching, such as a level one cache 711 and a level two cache 712, a processor core 713, and registers 714. The processor core 713 may include an arithmetic logic unit (ALU), a floating point unit (FPU), a digital signal processing core (DSP Core), or any combination thereof. A memory controller 715 may also be used with the processor 710, or in some implementations the memory controller 715 may be an internal part of the processor 710. It should be appreciated that the adaptable module described herein may be configured to communicatively couple with the example computing device 700.

Depending on the desired configuration, the system memory 720 may be of any type including but not limited to volatile memory (such as RAM), non-volatile memory (such as ROM, flash memory, etc.) or any combination thereof. System memory 720 may include an operating system 721, one or more applications 722, and program data 724. Application 722 may include adaptable module coupling algorithm 723 that is arranged to perform the functions as described herein including the functional blocks and/or actions described. Program Data 724 may include, among many information described, capable functionalities of defibrillator devices 725 for use with adaptable module coupling algorithm 723. In some example embodiments, application 722 may be arranged to operate with program data 724 on an operating system 721 such that implementations of an adaptable healthcare module may be provided as described herein. For example, apparatus described in the present disclosure may comprise all or a portion of computing device 700 and be capable of performing all or a portion of application 722 such that implementations of adaptable healthcare module may be provided as described herein. This described basic configuration is illustrated in FIG. 7 by those components within dashed line 701.

Computing device 700 may have additional features or functionality, and additional interfaces to facilitate communications between the basic configuration 701 and any required devices and interfaces. For example, a bus/interface controller 740 may be used to facilitate communications between the basic configuration 701 and one or more data storage devices 750 via a storage interface bus 741. The data storage devices 750 may be removable storage devices 751, non-removable storage devices 752, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 720, removable storage 751 and non-removable storage 752 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of device 700.

Computing device 700 may also include an interface bus 742 for facilitating communication from various interface devices (e.g., output interfaces, peripheral interfaces, and communication interfaces) to the basic configuration 701 via the bus/interface controller 740. Example output interfaces 760 may include a graphics processing unit 761 and an audio processing unit 762, which may be configured to communicate to various external devices such as a display or speakers via one or more A/V ports 763. Example peripheral interfaces 760 may include a serial interface controller 771 or a parallel interface controller 772, which may be configured to communicate with external devices such as input devices (e.g., keyboard, mouse, pen, voice input device, touch input device, etc.) or other peripheral devices (e.g., printer, scanner, etc.) via one or more I/O ports 773. An example communication interface 780 includes a network controller 781, which may be arranged to facilitate communications with one or more other computing devices 790 over a network communication via one or more communication ports 782. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 700 may also be implemented as a personal computer including both laptop computer and non-laptop computer configurations. In addition, computing device 700 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

Claimed subject matter is not limited in scope to the particular implementations described herein. For example, some implementations may be in hardware, such as employed to operate on a device or combination of devices, for example, whereas other implementations may be in software and/or firmware. Likewise, although claimed subject matter is not limited in scope in this respect, some implementations may include one or more articles, such as a signal bearing medium, a storage medium and/or storage media. This storage media, such as CD-ROMs, computer disks, flash memory, or the like, for example, may have instructions stored thereon, that, when executed by a computing device, such as a computing system, computing platform, or other system, for example, may result in execution of a processor in accordance with claimed subject matter, such as one of the implementations previously described, for example. As one possibility, a computing device may include one or more processing units or processors, one or more input/output devices, such as a display, a keyboard and/or a mouse, and one or more memories, such as static random access memory, dynamic random access memory, flash memory, and/or a hard drive.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. An adaptable healthcare module, comprising:
    a power supply coupled to one or more elements of the adaptable healthcare module;
    a processor coupled to the power supply, a memory, a coupling control module, a communicative coupling and a healthcare coupling;
    the memory configured to store at least one of patient data and physiological parameter data;
    an interface that is configured to mechanically, selectively engage with a first healthcare monitoring device such that the adaptable healthcare module is physically attached to the first healthcare monitoring device when in a coupled state;
    the communicative coupling configured to facilitate communication with at least one of the first healthcare monitoring device and a second healthcare monitoring device; and
    the healthcare coupling, the healthcare coupling communicatively coupled to the coupling control module and configured to at least one of receive physiological parameter data from one or more physiological sensors and cause the received physiological parameter data to be stored in the memory;
    the coupling control module configured to:
        transmit at least a portion of one or both of patient data and the physiological parameter data to the first healthcare monitoring device;
        cause the adaptable healthcare module to continue to collect physiological parameter data from the one or more physiological sensors when the adaptable healthcare module is decoupled from the first healthcare monitoring device, the collected physiological parameter data stored in the memory; and
        transmit at least a portion of one or both of the patient data and the stored physiological parameter data to the second healthcare monitoring device.

2. An adaptable healthcare module, comprising:
    a power supply configured to supply power to the adaptable healthcare module;
    a processor communicatively coupled to at least one of the power supply, a memory, a coupling control module, a communicative coupling and a healthcare coupling;
    the memory configured to store at least one of patient data and physiological parameter data;
    a mechanical interface configured to selectively engage with a first defibrillator or a second defibrillator, the engagement causing the adaptable healthcare module to be attached to the first defibrillator or the second defibrillator when coupled thereto;
    the communicative coupling configured to facilitate communication with at least one of the first defibrillator or the second defibrillator when coupled thereto;
    the healthcare coupling configured to receive physiological parameter data from one or more physiological parameter sensors; and
    the coupling control module configured to:
        transmit at least a portion of one or both of patient data and the physiological parameter data to a first defibrillator;
        cause the adaptable healthcare module to continue to collect physiological parameter data from the one or more physiological parameter sensors when the adaptable healthcare module is decoupled from the first defibrillator, the collected physiological parameter data stored in the memory; and
        transmit at least a portion of one or both of the stored patient data and the stored physiological parameter data to the second defibrillator.

3. The adaptable healthcare module of claim 2, wherein the healthcare coupling is wirelessly coupled to the one or more physiological parameter sensors.

4. The adaptable healthcare module of claim 2, wherein the healthcare coupling is coupled to the one or more physiological parameter sensors by a physical connection.

5. The adaptable healthcare module of claim 2, wherein the coupling control module is configured to transmit at least a portion of the patient data and the physiological parameter data to the first defibrillator, the coupling control module configured to retrieve the patient data from a remote patient data server.

6. The adaptable healthcare module of claim 2, wherein physiological parameter data is associated with a patient, and wherein the first defibrillator and the second defibrillator are configured to deliver one or both of treatment or monitoring to the patient.

7. The adaptable healthcare module of claim 6, wherein the one or both of treatment or monitoring of the first defibrillator includes at least a portion of capabilities of the one or both of treatment or monitoring of the second defibrillator.

8. The adaptable healthcare module of claim 2, wherein the coupling control module is further configured to transmit at least a portion of the patient data and the physiological parameter data to the second defibrillator.

9. The adaptable healthcare module of claim 2, wherein the coupling control module is further configured to retrieve the patient data from a remote patient data server and transmit at least a portion of the patient data and the physiological parameter data to the second defibrillator.

10. The adaptable healthcare module of claim 2, wherein the coupling control module is further configured to cause the adaptable healthcare module to continue to collect physiological parameter data from the one or more physiological parameter sensors when the adaptable healthcare module is coupled to the second defibrillator.

11. The adaptable healthcare module of claim 2, wherein the first defibrillator and the second defibrillator both have capabilities to administer defibrillation therapy.

12. The adaptable healthcare module of claim 2, further comprising a power source configured to power one or both of the healthcare coupling and the coupling control module.

* * * * *